US012594545B2

(12) United States Patent
Ong et al.

(10) Patent No.: US 12,594,545 B2
(45) Date of Patent: Apr. 7, 2026

(54) NANOSTRUCTURED HYBRID IRON-ZEOLITE CATALYSTS

(71) Applicants: AGENCY FOR SCIENCE, TECHNOLOGY AND RESEARCH, Singapore (SG); IHI CORPORATION, Tokyo (JP)

(72) Inventors: Sze Wei Daniel Ong, Singapore (SG); Luwei Chen, Singapore (SG); Chee Kok Poh, Singapore (SG); Jie Chang, Singapore (SG); Noriki Mizukami, Tokyo (JP); Yoshinori Izumi, Tokyo (JP); Hiroyuki Kamata, Tokyo (JP); Armando Borgna, Singapore (SG)

(73) Assignees: AGENCY FOR SCIENCE, TECHNOLOGY AND RESEARCH, Singapore (SG); IHI CORPORATION, Tokyo (JP)

( * ) Notice: Subject to any disclaimer, the term of this patent is extended or adjusted under 35 U.S.C. 154(b) by 742 days.

(21) Appl. No.: 17/782,332

(22) PCT Filed: Dec. 3, 2020

(86) PCT No.: PCT/SG2020/050716
§ 371 (c)(1),
(2) Date: Jun. 3, 2022

(87) PCT Pub. No.: WO2021/112767
PCT Pub. Date: Jun. 10, 2021

(65) Prior Publication Data
US 2023/0001389 A1      Jan. 5, 2023

(30) Foreign Application Priority Data

Dec. 3, 2019    (SG) ............................ 10201911594P

(51) Int. Cl.
| | |
|---|---|
| *B01J 23/78* | (2006.01) |
| *B01J 23/00* | (2006.01) |
| *B01J 29/08* | (2006.01) |
| *B01J 29/40* | (2006.01) |
| *B01J 29/85* | (2006.01) |
| *B01J 35/45* | (2024.01) |
| *B01J 35/70* | (2024.01) |
| *B01J 37/03* | (2006.01) |
| *B01J 37/08* | (2006.01) |
| *B01J 37/18* | (2006.01) |
| *C07C 1/04* | (2006.01) |

(52) U.S. Cl.
CPC ............. *B01J 23/78* (2013.01); *B01J 23/005* (2013.01); *B01J 29/084* (2013.01); *B01J 29/40* (2013.01); *B01J 29/85* (2013.01); *B01J 35/45* (2024.01); *B01J 35/70* (2024.01); *B01J 37/031* (2013.01); *B01J 37/08* (2013.01); *B01J 37/18* (2013.01); *C07C 1/043* (2013.01); *C07C 1/0445* (2013.01); *B01J 2235/00*

(2024.01); *B01J 2235/15* (2024.01); *B01J 2235/30* (2024.01); *C07C 2523/78* (2013.01); *C07C 2529/08* (2013.01); *C07C 2529/40* (2013.01); *C07C 2529/85* (2013.01)

(58) Field of Classification Search
CPC ........ B01J 23/78; B01J 23/005; B01J 29/084; B01J 29/40; B01J 29/85; B01J 35/23; B01J 37/031; B01J 37/08; B01J 37/18; C07C 1/043; C07C 1/0445; C07C 2523/78; C07C 2529/08; C07C 2529/40; C07C 2529/85
See application file for complete search history.

(56) References Cited

U.S. PATENT DOCUMENTS

| | | | |
|---|---|---|---|
| 4,518,707 | A | 5/1985 | Soled et al. |
| 4,849,575 | A | 7/1989 | Lewis |
| 2018/0111117 | A1 | 4/2018 | Xu et al. |

FOREIGN PATENT DOCUMENTS

| | | | | |
|---|---|---|---|---|
| CN | 101396662 A | 4/2009 | | |
| JP | S61-502544 | 11/1986 | | |
| JP | S61-502897 | 12/1986 | | |
| JP | H02-000121 | 1/1990 | | |
| JP | 2018-524156 A | 8/2018 | | |
| WO | WO-1986/00295 A1 | 1/1986 | | |
| WO | WO-1986/00297 A1 | 1/1986 | | |
| WO | WO-2019155476 A1 * | 8/2019 | ............... | C02F 1/70 |

OTHER PUBLICATIONS

Greenwood, N.N. Earnshaw, A.. "Chemistry of the Elements (2nd Edition)" Elsevier, 1997, 839-852, 14 pages. Retrieved from https://app.knovel.com/hotlink/toc/id:kpCEE00006/chemistry-elements-2nd/chemistry-elements-2nd (Year: 1997).*

(Continued)

*Primary Examiner* — Anthony J Zimmer
*Assistant Examiner* — Abdul-Rahman Yusuf Waleed Smari
(74) *Attorney, Agent, or Firm* — Marshall, Gerstein & Borun LLP

(57) ABSTRACT

The present invention relates to a hybrid iron nanoparticle catalyst comprising: i) 1 to 50 wt. % nanoparticles comprising iron and at least one of a metal M selected from the group consisting of alkali metals, alkaline earth metals, transition metals of groups 3 to 7 and 9 to 11 of the Periodic Table of Elements, lanthanides and combinations of M thereof; and ii) 50 to 99 wt. % of an aluminosilicate or silicoaluminophosphate zeolite, based on the total weight of the catalyst, wherein said nanoparticle has a diameter of about 2 to 50 nm. The present invention also relates to a method of preparing the hybrid iron nanoparticle catalyst and a process for the production of light olefins using the hybrid iron nanoparticle catalyst.

11 Claims, 8 Drawing Sheets

(56) References Cited

OTHER PUBLICATIONS

Wang et al., "Particle-based detection of DNA hybridization using electrochemical stripping measurements of an iron tracer" Analytica Chimica Acta 482, Apr. 2003, 149-155 (Year: 2003).*

Wei et al., "Directly Converting $CO_2$ Into a Gasoline Fuel", Nature Communications, vol. 8, May 2, 2017, 9 pages.

Martínez et al., "The Influence of ZSM-5 Zeolite Composition and Crystal Size on the in situ Conversion of Fischer-Tropsch Products Over Hybrid Catalysts", Applied Catalysis A: General, vol. 294, Sep. 6, 2005, pp. 251-259.

Zhu et al., "Enhancing the Light Olefin Selectivity of an Iron-based Fischer-Tropsch Synthesis Catalyst by Modification With CTAB", RSC Adv., vol. 8, No. 56, Sep. 14, 2018, pp. 32073-32083.

Xu et al., "Synthesis of Aromatics From Syngas Over $FeMnK/SiO_2$ and HZSM-5 Tandem Catalysts", Molecular Catalysis, vol. 454, Jun. 13, 2018, pp. 104-113.

Search Report in International Application No. PCT/SG2020/ 050716 dated Feb. 22, 2021, 4 pages.

Office Action in JP Application No. 2022-533070 dated Mar. 5, 2024, 6 pages.

Written Opinion in SG Application No. 11202250034X dated Mar. 13, 2024, 11 pages.

* cited by examiner

[Fig. 1]
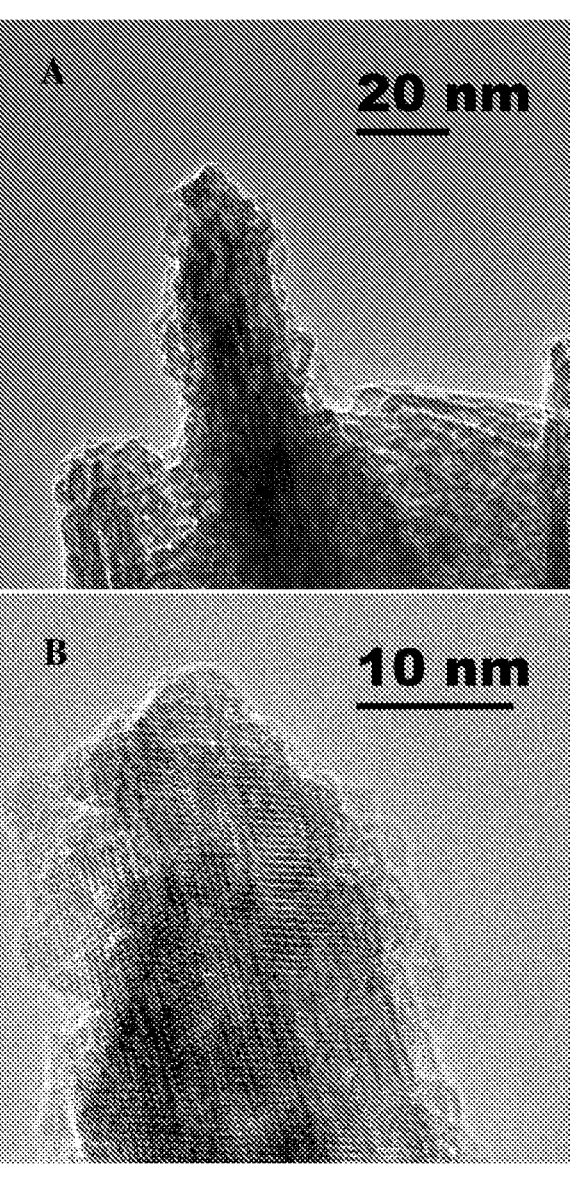

[Fig. 2A]
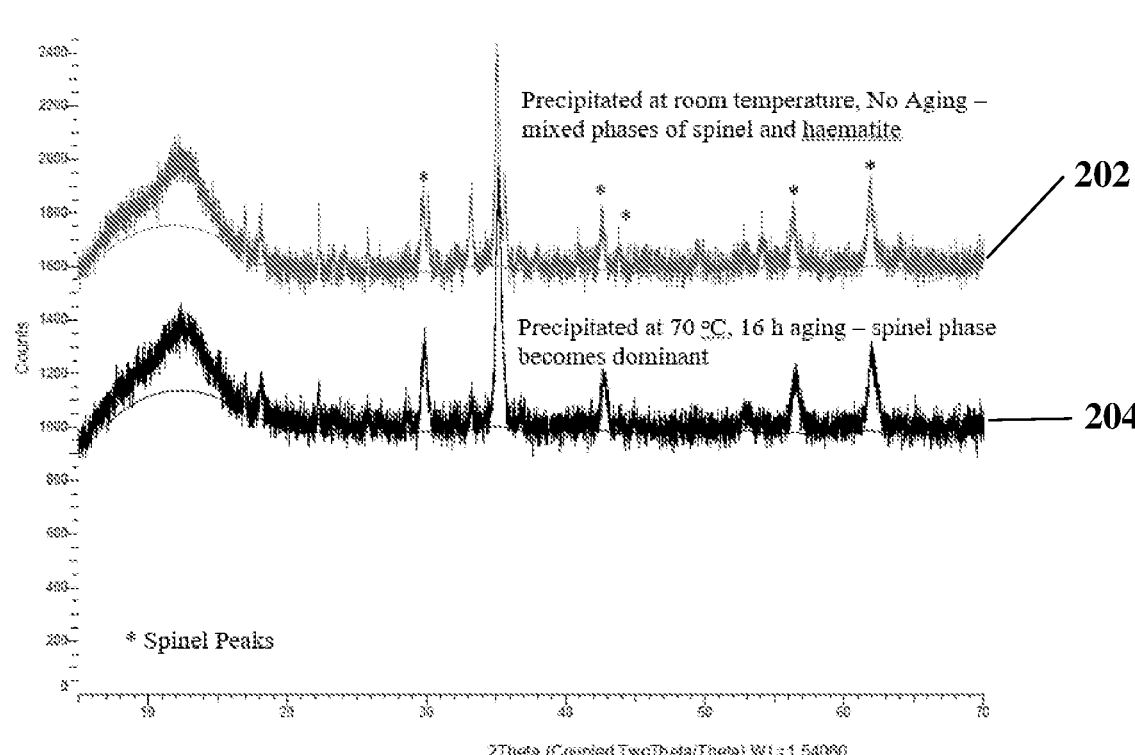
[Fig. 2B]
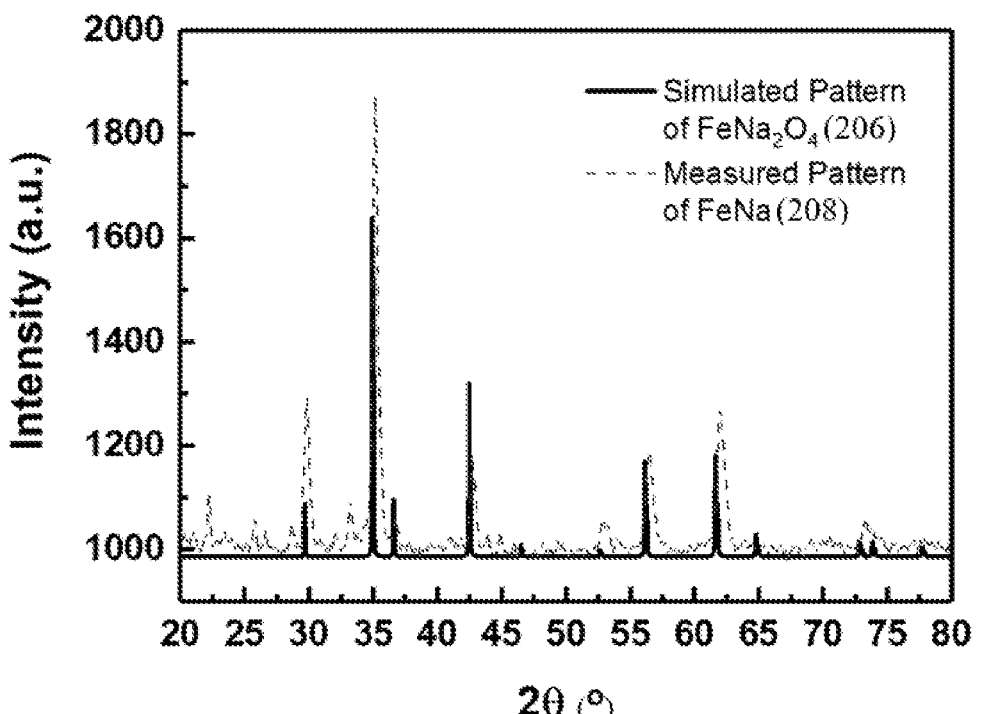

[Fig. 3]
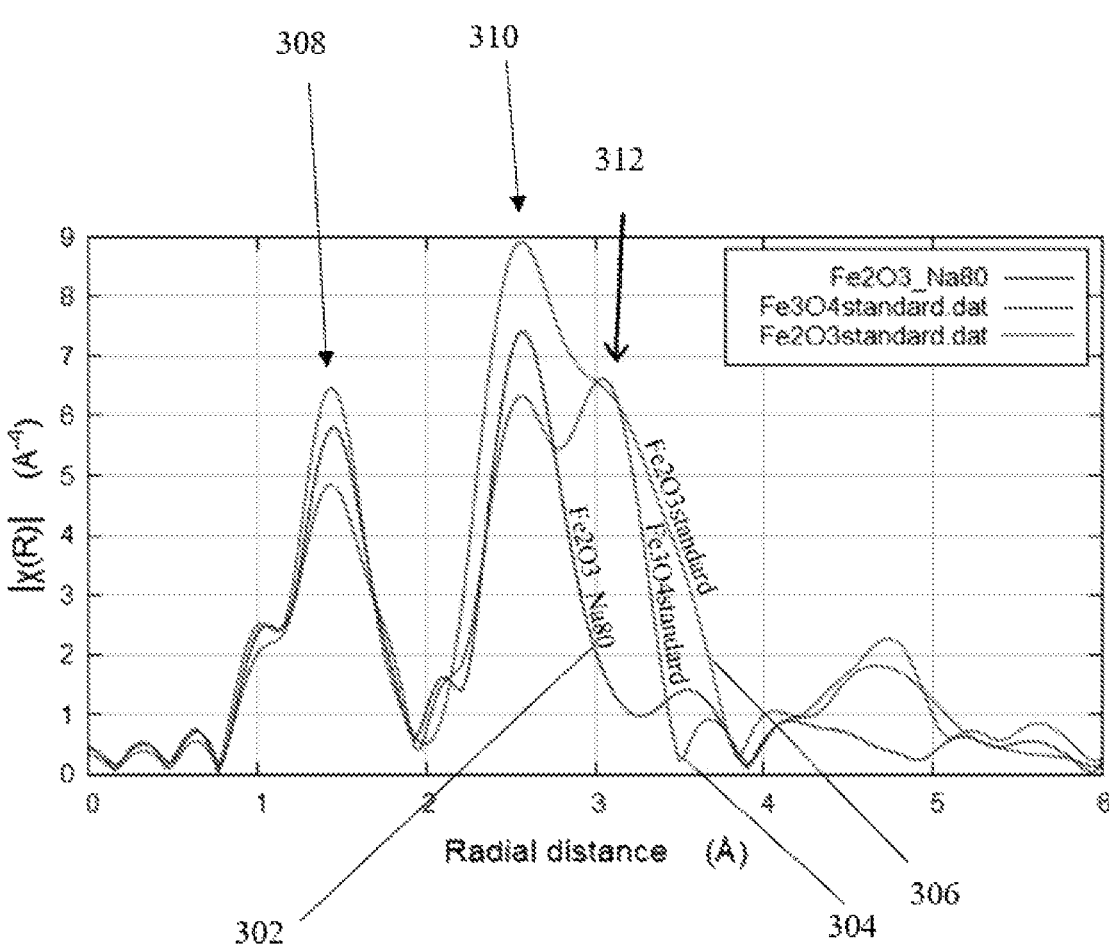

[Fig. 4]
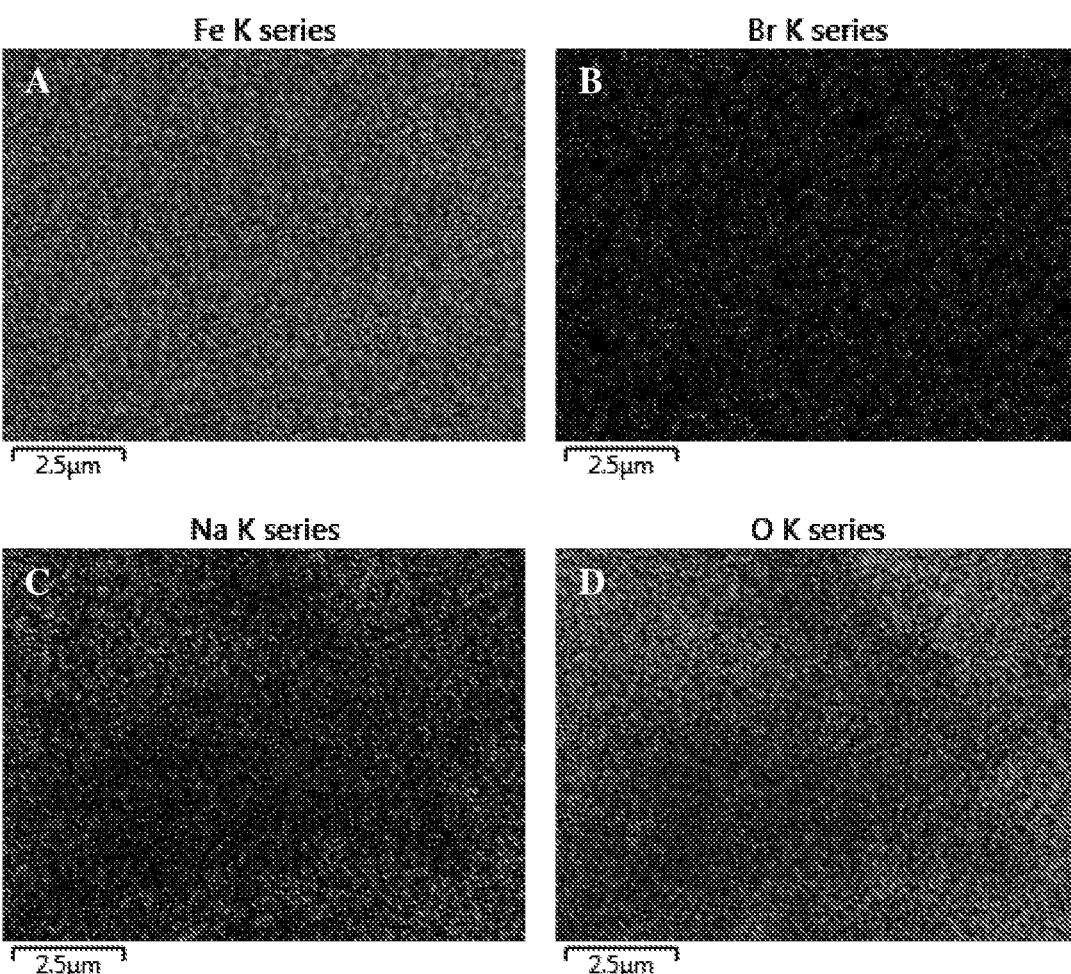

[Fig. 5]
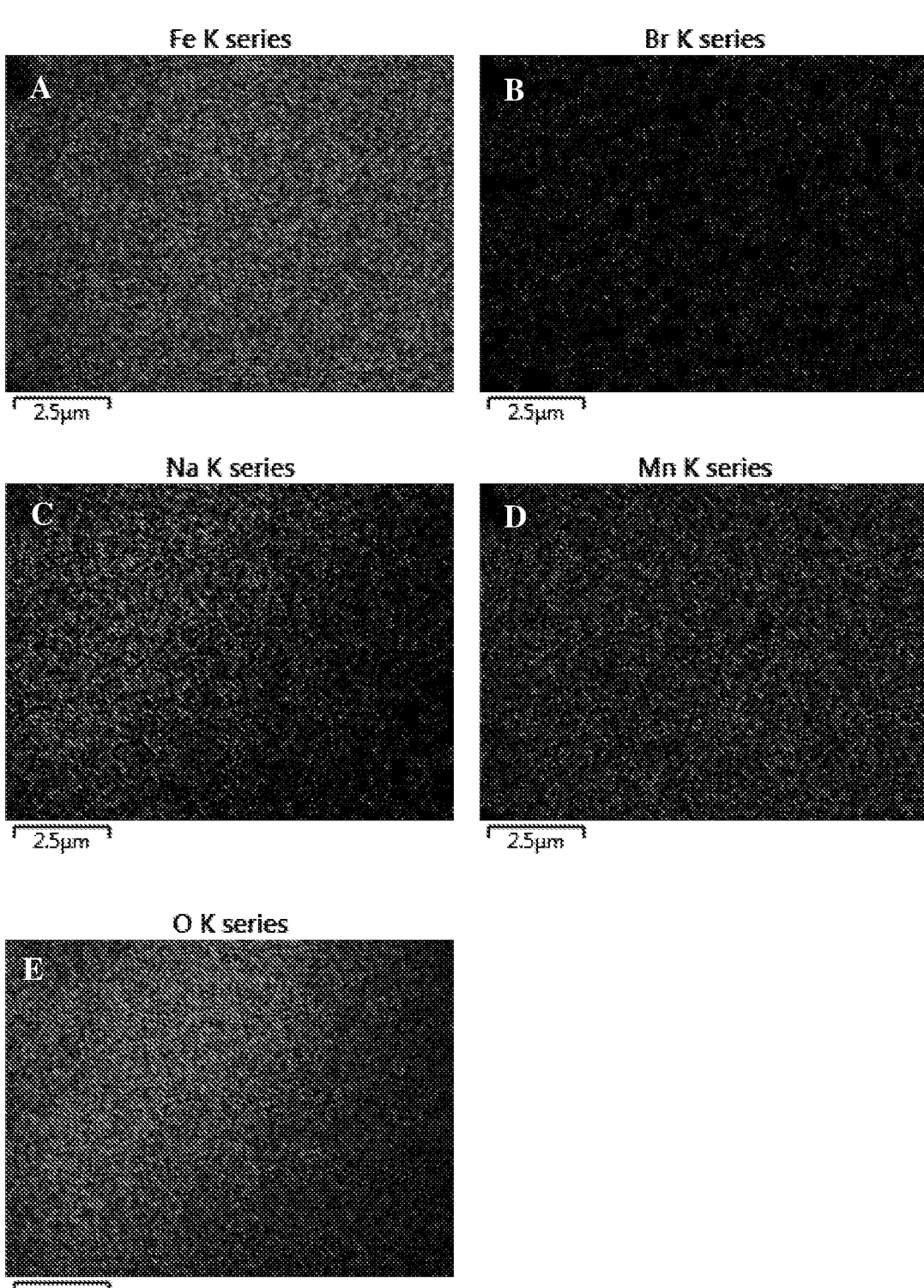

[Fig. 6]
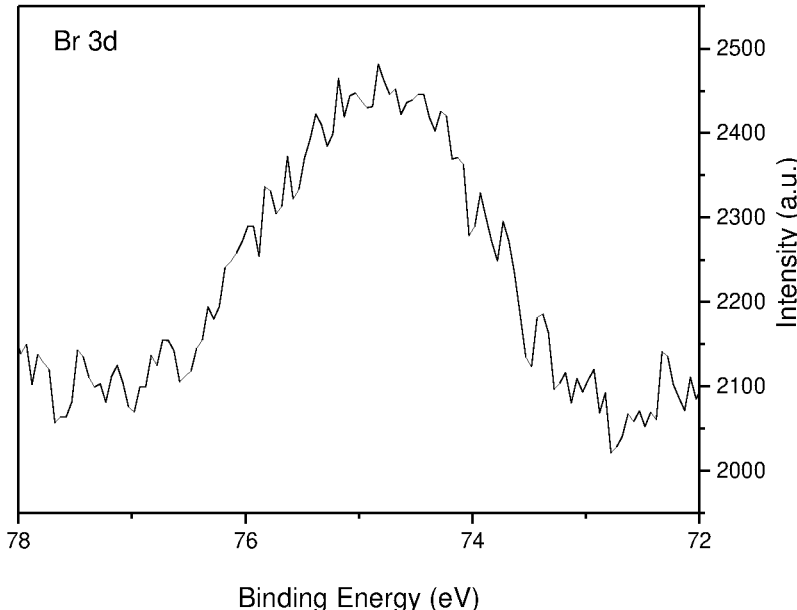
[Fig. 7]
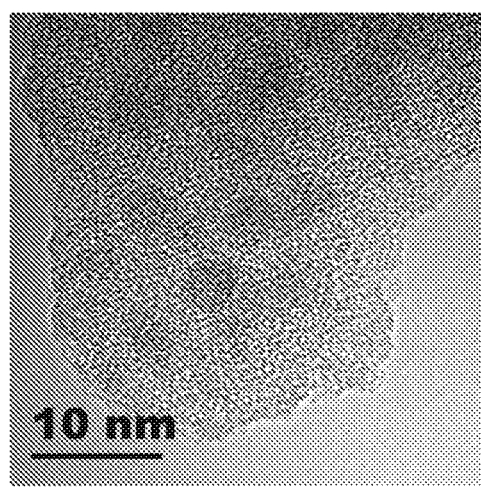

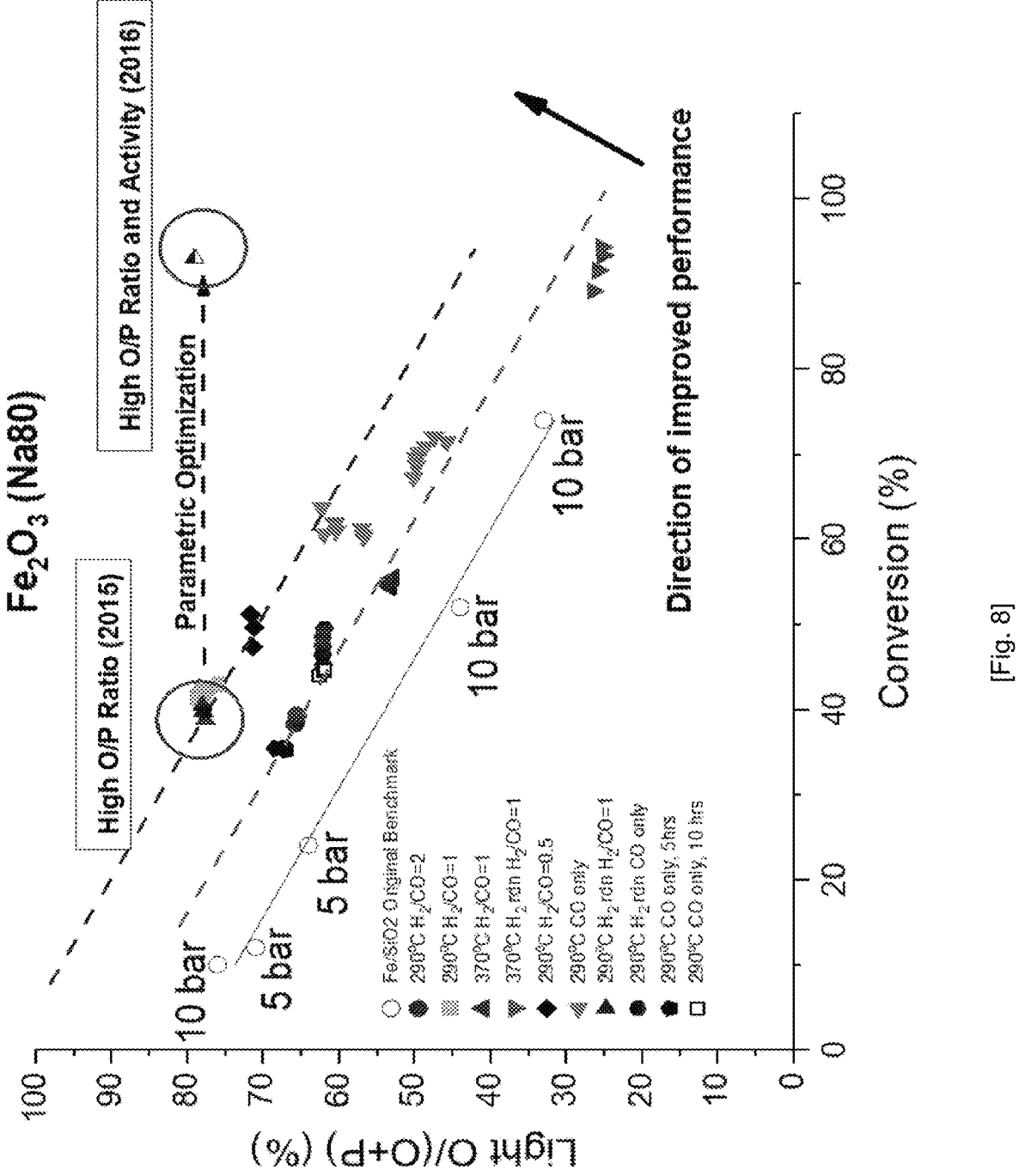
[Fig. 8]

[Fig. 9]
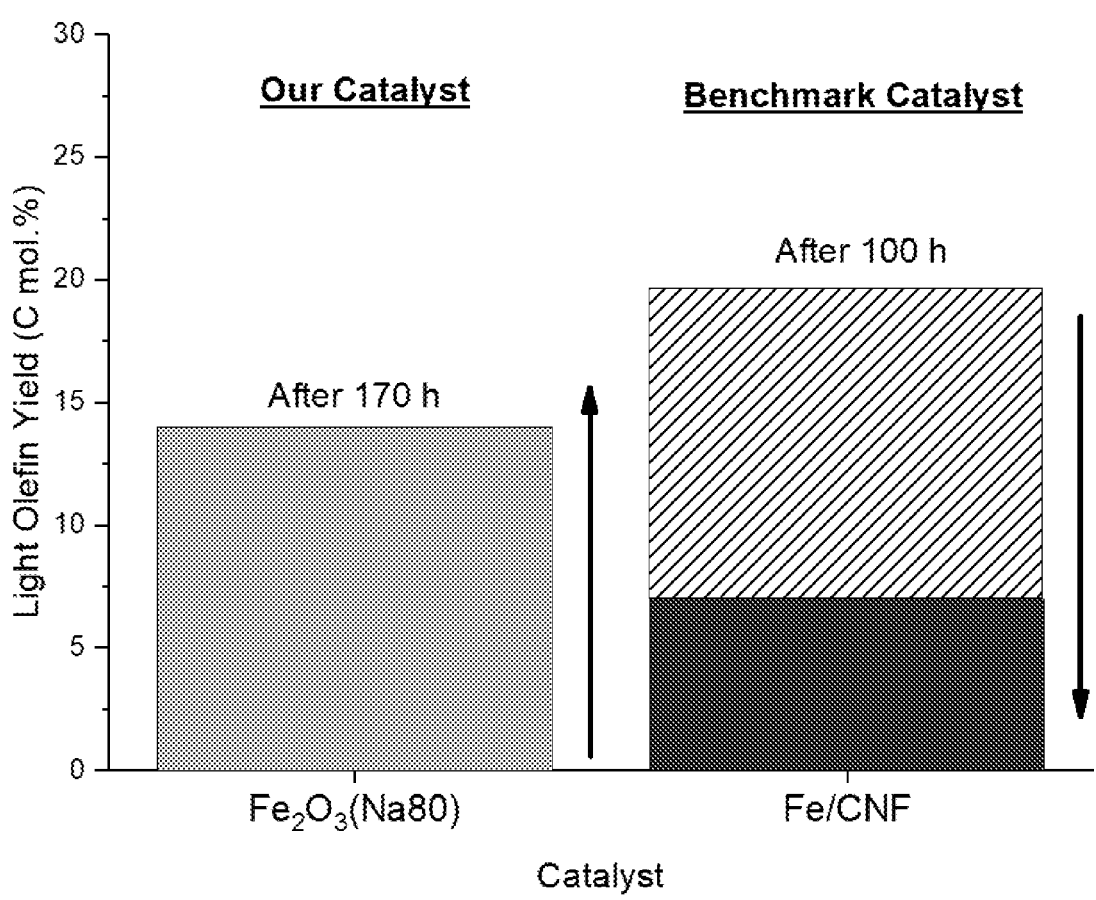

NANOSTRUCTURED HYBRID IRON-ZEOLITE CATALYSTS

TECHNICAL FIELD

The present invention relates to the synthesis of nanostructured hybrid Fe-zeolite catalysts that optimizes light olefin selectivity and yield. Specific examples are demonstrated through one-pot precipitation reactions and physical mixing with zeolites.

BACKGROUND ART

Fischer-Tropsch Synthesis is a collection of chemical processes which use CO and $H_2$ as feedstock to produce longer-chain hydrocarbons. These processes usually take place over catalysts based on Co, Fe, Ru and even Ni and Re. However, conventional catalysts and processes are known to produce mainly paraffins and/or gasoline product fractions, with low yield for light olefins.

Recent interest has re-surfaced on the use of Fe in the direct Fischer-Tropsch to olefin (FTO) process due to its lower cost compared to other materials, as well as its promising selectivity to light olefin production (C2-C4). In particular, Fe-based catalysts promoted with elements such as alkali metals, alkali earth metals, transition metals and lanthanides have shown various enhancements, such as active site dispersion, faster activation, suppression of methane and improvement to olefinicity of hydrocarbon products.

Effective Fe-based catalysts for FTO require that the selectivity for light olefins be high and that for $CH_4$ and C5+ (hydrocarbons comprising 5 or more carbons) to be low. However, known Fe-based catalysts have only been able to produce mainly paraffins and/or gasoline product fractions. Further, for known Fe-based catalysts, the product distribution is limited by the so-called Anderson-Schulz-Flory (ASF) theory, which shows that it is difficult to maximize the selectivity for C2-C4 olefins without concurrently increasing the selectivity for $CH_4$ and/or C5+.

There is therefore a need to provide a catalyst and a method of use thereof that overcomes or at least ameliorates, one or more of the disadvantages described above.

SUMMARY

In an aspect, there is provided a hybrid iron nanoparticle catalyst comprising:

i) 30 to 70 wt. % of nanoparticles comprising iron and at least one of a metal M selected from the group consisting of alkali metals, alkaline earth metals, transition metals of groups 3 to 7 and 9 to 11 of the Periodic Table of Elements, lanthanides and combinations of M thereof; and ii) 70 to 30 wt. % of an aluminosilicate or silicoaluminophosphate zeolite, based on the total weight of the catalyst wherein said nanoparticle has a diameter of about 2 to 50 nm, and the total wt. % of the nanoparticles and zeolite is 100 wt. %.

Advantageously, the presently described hybrid iron nanoparticle catalyst may demonstrate improved activity over the Fischer Tropsch iron catalysts known in the art. High selectivity and conversion of the gas comprising hydrogen and an oxide of carbon to the desired light olefins may be achieved utilizing the catalysts as described herein. This may be attributed to the high percentage of the alkali metals, alkaline earth metals, transition metals or lanthanide in the catalyst, as well as the porous nature of the zeolite.

In an example, the presently described catalyst may adopt a spinel crystalline phase.

Advantageously, nanoparticle catalysts having the spinel phase may demonstrate improved conversion of carbon monoxide or carbon dioxide to light olefins, particularly light olefins comprising 2 to 4 carbon atoms, with up to 24 mol. C % improvement compared to conventional catalysts. The improved yields may be attributed to the crystalline spinel phase of the nanoparticle catalysts.

In another aspect, there is provided a method of preparing a hybrid nanoparticle iron catalyst, the method comprising i) mixing an iron salt with an aqueous surfactant to form a mixture;

ii) adding a basic salt solution comprising a salt of an element selected from the group consisting of alkali metals, alkaline earth metals, transition metals of groups 3 to 7 or 9 to 11 of the Periodic Table of Elements, lanthanides, and combinations of elements thereof; to the mixture of step (i) to form a precipitate;

iii) heating the precipitate of step (ii) in the presence of air and oxygen; and iv) mixing the precipitate of step (iii) with an aluminosilicate or a silicoaluminophosphate zeolite to yield a hybrid iron catalyst.

Advantageously, the presently disclosed method of preparing the hybrid iron nanoparticle catalyst may involve the co-precipitation of an iron nanoparticle catalyst with a basic salt solution. The co-precipitation method may enable a high concentration of the alkali metal, alkaline earth metal, transition metal of groups 3 to 7 or 9 toll of the Periodic Table of Elements, lanthanides, and combinations of elements thereof to be included in the nanoparticle. Such iron nanoparticles may surprisingly demonstrate enhanced catalytic activity for the conversion of carbon monoxide or carbon dioxide to light olefins via a Fischer Tropsch reaction. Along with the improved conversion of the carbon monoxide or carbon dioxide gas, the catalyst may also demonstrate selectivity for light olefins comprising 2 to 4 carbon atoms over methane and long chain paraffins.

Further advantageously, the hybrid iron catalyst and zeolite disclosed herein may also reduce the activation time of the catalyst in the Fischer-Tropsch reaction, with an activation speed of 2 to 16 hours as compared to conventional catalysts with induction times of 40 to 100 hours. As such, high yields of the light olefin may be achieved within a shorter period of time, without compromising the selectivity of the catalysts for the C2-C4 light olefins.

In another aspect, there is provided a process for the production of light olefins, the process comprising the step of:

i) heating the catalyst as defined above in the presence of a gas comprising one or more oxides of carbon and hydrogen to activate said catalyst; and ii) contacting said activated catalyst of step (i) with a gas stream comprising one or more oxides of carbon and hydrogen to partially or fully convert said one or more oxides of carbon to said light olefins, said light olefins comprising between 2 to 4 carbon atoms, wherein methane is substantially absent from said light olefins, or constitutes less than 20% of said light olefins.

Advantageously, the process may facilitate the presently disclosed catalysts to achieve a high conversion of oxides of carbon to hydrocarbons. In particular, the catalysts disclosed herein may favor the formation of short chain olefins over paraffins, particularly light olefins comprising 2 to 4 carbon atoms. Such light olefins are also selectively formed over methane using the presently disclosed iron-zeolite catalysts. The high conversion and selectivity of the iron-zeolite catalysts in the disclosed process may be attributed to the spinel phase of the iron nanoparticles which are particularly active for the formation of light olefins from oxides of carbons. Further advantageously, the zeolite present in the catalyst may act to decompose C5+ olefins to improve the selectivity of the catalyst for light olefins.

Surprisingly, the iron-zeolite catalysts may have a reduced activation time in the disclosed process as compared to similar iron-zeolite catalysts known in the art. This may advantageously allow a high yield of light olefins to be obtained within a shorter reaction time.

Definitions

The following words and terms used herein shall have the meaning indicated:

The term "promoted", in the context of the present disclosure, refers to the enhancement of catalytic activity or significant changes in the catalytic properties of a catalyst in the presence of an additional metal ion, preferably selected from the group consisting of alkali metals, alkaline earth metals, transition metals of groups 3 to 7 or 9 to 11 of the Periodic Table of Elements, or lanthanides, and combinations thereof. The words "promotion" and "promoter" should be construed accordingly.

The term "spinel crystalline phase", in the context of the present disclosure, refers to a class of minerals of general formulation $AB_2X_4$, with the X anions (typically chalcogens, like oxygen and sulfur) arranged in a close-packed lattice and the cations A and B occupying some or all of the octahedral and tetrahedral sites in the lattice.

The term "light olefin", in the context of the present disclosure, refers to olefins or alkenes that comprise 2 to 4 carbon atoms. Light olefin may therefore refer to ethylene, propene and/or butene, whereby the butene may include but-1-ene, (2Z)-but-2-ene, (2E)-but-2-ene and 2-methyl-prop-1-ene.

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and sub-generic groupings falling within the generic disclosure also form part of the disclosure. This includes the generic description of the embodiments with a proviso or negative limitation removing any subject matter from the genus, regardless of whether or not the excised material is specifically recited herein.

DETAILED DISCLOSURE OF OPTIONAL EMBODIMENTS

The catalyst and method proposed herein combines zeolites with nanostructured hybrid Fe-zeolite catalysts through physical mixing, in order to enhance the activity, selectivity and by extension, yield of light olefins.

Specifically, the present disclosure relates to methods of synthesizing promoted nano-particulate iron-based catalyst for use in the Fischer-Tropsch to Olefin reaction for high C2-C4 linear alpha-olefin yield of up to 20 C mol. % per pass.

There is provided a catalyst comprising:

30 to 70 wt. % of nanoparticles comprising iron and at least one of a metal M selected from the group consisting of alkali metals, alkaline earth metals, transition metals of groups 3 to 7 or 9 toll of the Periodic Table of Elements, lanthanides and combinations of M thereof;

70 to 30 wt. % of an aluminosilicate or silicoaluminophosphate zeolite, based on the total weight of the catalyst wherein said nanoparticle has a diameter of about 2 to 50 nm, and the total wt. % of the nanoparticles and zeolite is 100 wt. %.

The catalyst may comprise about 30 to about 70 wt. %, about 30 to about 40 wt. %, about 30 to about 50 wt. %, about 30 to about 60 wt. %, about 40 to about 50 wt. %, about 40 to about 60 wt. %, about 40 to about 70 wt. %, about 50 to about 60 wt. %, about 50 to about 70 wt. % or about 60 to about 80 wt. % nanoparticles.

The catalyst may comprise about 30 to about 70 wt. %, about 30 to about 40 wt. %, about 30 to about 50 wt. %, about 30 to about 60 wt. %, about 40 to about 50 wt. %, about 40 to about 60 wt. %, about 40 to about 70 wt. %, about 50 to about 60 wt. %, about 50 to about 70 wt. % or about 60 to about 80 wt. % zeolite.

The total wt. % of the nanoparticles and zeolites is 100 wt. %.

The nanoparticle may have a diameter in the range of about 2 nm to 50 nm, about 2 nm to about 5 nm, about 2 nm to about 10 nm, about 2 nm to about 20 nm, about 5 nm to about 10 nm, about 5 nm to about 20 nm, about 5 nm to about 50 nm, about 10 nm to about 20 nm, about 10 nm to about 50 nm, or about 20 nm to about 50 nm.

The metal M may comprise about 10 to 50 wt. % based on the weight of the iron nanoparticle catalyst, or about 10 to about 20 wt. %, about 10 to about 30 wt. %, about 10 to about 40 wt. %, about 20 to about 30 wt. %, about 20 to about 40 wt. %, about 20 to about 50 wt. %, about 30 to about 40 wt. %, about 30 to about 50 wt. %, or about 40 to about 50 wt. %, more preferably about 10% based on the weight of the iron nanoparticle catalyst.

The nanoparticles may adopt a spinel crystalline phase.

The formula of the catalyst having a spinel crystalline phase may have the formula $FeM_2O_4$.

The metal M may be selected from the group consisting of alkali metals, alkaline earth metals, transition metals of groups 3 to 7 or 9 to 11 of the Periodic Table of Elements, lanthanides, and combinations of M thereof. The alkali metal may be selected from the group consisting of lithium, sodium, potassium, rubidium, and caesium. The alkaline earth metal may be selected from the group consisting of beryllium, magnesium, calcium, strontium, and barium. The group 3 transition metal may be selected from the group consisting of scandium and yttrium. The group 4 transition metal may be selected from the group consisting of titanium, zirconium, and hafnium. The group 5 transition metal may be selected from the group consisting of vanadium, niobium and tantalum. The group 6 transition metal may be selected from the group consisting of chromium, molybdenum and tungsten. The group 7 transition metal may be selected from the group consisting of manganese, technetium and rhenium. The group 9 transition metal may be selected from the group consisting of cobalt, rhodium and iridium. The group 10 transition metal may be selected from the group consisting of nickel, palladium and platinum. The group 11 transition metal may be selected from the group consisting of copper, silver and gold. The lanthanide may be selected from the group consisting of lanthanum, cerium, praseodymium, neodymium, promethium, samarium, europium, gadolinium, terbium, dysprosium, holmium, erbium, thulium, ytterbium and lutetium.

The metal M may be an alkali metal. The metal M may be sodium.

The zeolite may be an aluminosilicate zeolite. The zeolite may be a pentasil or faujasite zeolite.

The zeolite may be selected from the group consisting of zeolite X, ZSM-5, zeolite Y, ZSM-12, ZSM-22, and HY zeolite. The zeolite may be ZSM-5 or HY zeolite.

ZSM-5 may have a chemical formula $Na_nAl_nSi_{96-n}O_{192}.16H_2O$ (0<n<27), Zeolite Y may have a chemical formula $Al_2O_5Si$, ZSM-12 may have a chemical formula $|Na_x (H_2O)_4|_2[Al_xSi_{28-x}O_{56}]_2$-(x<2.5), ZSM-22 may have a chemical formula $|Na_n (H_2O)_4|[Al_xSi_{24-x}O_{48}]$ (x<2). Both Zeolite X and Y may have same the basic formula $|(Ca,Mg,Na_2)_{29} (H_2O)_{240}|[Al_{58}Si_{134}O_{384}]$, wherein Zeolite Y may have a 1.5 times higher Si/Al ratio. Zeolite HY may be the Zeolite Y in H+ form whereby Ca, Mg or Na may be replaced.

The mole ratio of alumina to silica in the zeolite may be about 1:2 to about 1:90, or about 1:5 to about 1:90, or about 1:10 to about 1:90, or about 1:15 to about 1:90, or about 1:20 to about 1:90, or about 1:25 to about 1:90, or about 1:30 to about 1:90, or about 1:35 to about 1:90, or about 1:40 to about 1:90, or about 1:45 to about 1:90, or about 1:50 to about 1:90, or about 1:55 to about 1:90, or about 1:60 to about 1:90, or about 1:65 to about 1:90, or about 1:70 to about 1:90, or about 1:75 to about 1:90, or about 1:75 to about 1:85, or more preferably about 1:80.

The zeolite may be a silicoaluminophosphate zeolite. The silicoaluminophosphate may be SAPO 11 or SAPO 34. SAPO 11 may have a chemical formula $H_xSi_xAl_{20}P_{20-x}O_{80}$ (x=0-4) and SAP-34 may have a chemical formula $|Ca_6 (H_2O)_{40}|_{1/3} [Al_{12}Si_{24}O_{72}]_{1/3}$.

The weight ratio of the zeolite to the iron nanoparticle may be about 1:0.5 to about 1:10, or about 1:0.5 to about 1:8, or about 1:0.5 to about 1:6, or about 1:0.5 to about 1:4, or about 1:0.5 to about 1:3, or about 1:0.5 to about 1:2, or more preferably about 1:1.

The iron nanoparticles may further comprise an oxide of a halogen. The halogen may be bromine.

The oxide of the halogen may be present in an amount of about 0.1 to about 50 wt. %, or about 0.1 to about 45 wt. %, or about 0.1 to about 40 wt. %, or about 0.1 to about 35 wt. %, or about 0.1 to about 30 wt. %, or about 0.1 to about 25 wt. %, or about 0.1 to about 20 wt. % based on the weight of the nanoparticles.

The iron nanoparticles may exhibit an X-ray diffraction diagram as shown in FIG. 2B, with prominent diffraction peaks at 2θ=29.5°, 35°, 37°, 42.5°, 56.2°, and 62°.

The iron nanoparticle catalyst may exhibit an extended x-ray absorption fine structure analysis spectrum as shown in FIG. 3. The Fe—O coordination peak (308) may be found at a radial distance of 1.4 Å, while the first Fe—Fe coordination peak (310) may be found at 2.6 Å. The second Fe—Fe coordination peak (312) may be found at around 3.1 Å, which is typical for $Fe_3O_4$ (304) and existed as shoulder for $Fe_2O_3$ (306) due to less Fe in the chemical composition. The lack of this peak for FeNa ($Fe_2O_3$—Na) (302) may be an indication that it has a chemical formula $FeNa_2O_4$, where the Fe atoms are replaced by Na atoms. Throughout this disclosure, FeNa may be used interchangeably with $Fe_2O_3$—Na.

The iron nanoparticles may further comprise a transition metal of groups 3 to 7 or 9 to 11 of the Periodic Table of Elements. The transition metal may be selected from groups 7 or 10. The transition metal may be manganese.

The molar ratio of iron to the transition metal may be about 1:1 to about 50:1, or about 1:1 to about 40:1, or about 1:1 to about 30:1, or about 1:1 to about 20:1, or about 1:1 to about 18:1, or about 1:1 to about 16:1, or about 1:1 to about 14:1, or about 1:1 to about 12:1, or about 2:1 to about 12:1, or about 3:1 to about 12:1, or about 4:1 to about 12:1, or about 5:1 to about 12:1, or about 6:1 to about 12:1, or about 8:1 to about 12:1, or about 8:1 to about 10:1, more preferably about 9:1.

The iron nanoparticles may further comprise a $SiO_2$ matrix.

There is also provided a method of preparing a hybrid nanoparticle iron catalyst, the method comprising the steps of:

mixing an iron salt with an aqueous surfactant to form a mixture;

adding a basic salt solution comprising a salt of an element selected from the group consisting of alkali metals, alkaline earth metals, transition metals of groups 3 to 7 or 9 to11 of the Periodic Table of Elements, lanthanides and combinations of elements thereof; to the mixture of step (i) to form a precipitate;

heating the precipitate of step (ii) in the presence of air and oxygen; and mixing the precipitate of step (iii) with an aluminosilicate or a silicoaluminophosphate zeolite to yield a hybrid iron catalyst.

The salt of the element may comprise hydroxide, carbonate or bicarbonate anions.

The salt of the element may comprise an alkali metal cation.

The salt of the element may be sodium salt.

The molar ratio of the iron to the element of the basic salt may be about 1:2 to about 1:25, preferably about 1:2 to about 1:20, or about 1:2 to about 1:18, or about 1:2 to about 1:16, or about 1:2 to about 1:15, or about 1:2 to about 1:14, or about 1:2 to about 1:13, or about 1:2 to about 1:12, or about 1:2 to about 1:11, or about 1:2 to about 1:10, or about 1:3 to about 1:10, more preferably about 1:4 to 1:10.

The mole ratio of alumina to silicate in the zeolite may be about 1:2 to about 1:90, or about 1:5 to about 1:90, or about 1:10 to about 1:90, or about 1:15 to about 1:90, or about 1:20 to about 1:90, or about 1:25 to about 1:90, or about 1:30 to about 1:90, or about 1:35 to about 1:90, or about 1:40 to about 1:90, or about 1:45 to about 1:90, or about 1:50 to about 1:90, or about 1:55 to about 1:90, or about 1:60 to about 1:90, or about 1:65 to about 1:90, or about 1:70 to about 1:90, or about 1:75 to about 1:90, or about 1:75 to about 1:85, or more preferably about 1:80.

The heating step may be carried out at a temperature of about 300° C. to about 600° C., or about 350° C. to about 600° C., or about 400° C. to about 600° C., or about 450° C. to about 600° C., or about 500° C. to about 600° C., or about 500° C. to about 580° C., or about 500° C. to about 560° C., or about 500° C. to about 550° C., more preferably about 550° C.

The heating step may be carried out for about 1 to about 10 hours, or about 1 to about 8 hours, or about 1 to 6 about hours, or about 1 to about 5 hours, or about 1 to about 4 hours, or about 1 to about 3 hours, or about 1 to about 2 hours, more preferably about 2 hours.

The iron salt may be an iron (II) or iron (III) salt.

The iron salt may comprise an anion selected from the group consisting of nitrate, chloride, fluoride, bromide, iodide, phosphate, pyrophosphate and perchlorate.

The iron salt may be iron (III) nitrate.

The surfactant may be an ionic surfactant.

The surfactant may comprise an anion selected from the group consisting of: halides, sulfonates, sulfates, phosphates and carboxylates.

The surfactant may comprise a halide anion. The surfactant may comprise fluoride, chloride, bromide or iodide anion.

The surfactant may comprise a bromide anion.

The surfactant may be selected from the group consisting of cetrimonium bromide, pluronic F-127 which may have a chemical formula $(C_3H_6O \cdot C_2H_4O)x$, polyethylene glycol 400 which may have a chemical formula $C_{2n}H_{4n+2}O_{n+1}$ (n=8.2 to 9.1) and any mixture thereof.

The molar ratio of iron to the surfactant may be about 1:0.5 to about 1:15, or about 1:0.5 to about 1:12, or about 1:0.5 to about 1:10, or about 1:0.5 to about 1:8, or about 1:0.5 to about 1:6, or about 1:0.5 to about 1:4, or about 1:0.5 to about 1:2, or more preferably about 1:1.

The method may further comprise, prior to step (iii), the steps of:

collecting the precipitated nanoparticle catalyst; and drying said precipitated nanoparticle catalyst in air.

The collection of the precipitated nanoparticle catalyst may be by centrifugation and/or filtration.

The method may further comprise, prior to step (ii), the step of adding a solution of a salt of a transition metal to the mixture of step (i).

The molar ratio of iron to the transition metal may be about 1:1 to about 50:1, or about 1:1 to about 40:1, or about 1:1 to about 30:1, or about 1:1 to about 20:1, or about 1:1 to about 18:1, or about 1:1 to about 16:1, or about 1:1 to about 14:1, or about 1:1 to about 12:1, or about 2:1 to about 12:1, or about 3:1 to about 12:1, or about 4:1 to about 12:1, or about 5:1 to about 12:1, or about 6:1 to about 12:1, or about 8:1 to about 12:1, or about 8:1 to about 10:1, more preferably about 9:1.

The method may further comprise:

prior to step ii), introducing a solution of a silicate to the mixture of step (i).

The silicate may comprise alkoxy groups of 2 to 15 carbon atoms, preferably 2 to 12 carbon atoms, 2 to 10 carbon atoms, or 2 to 8 carbon atoms, or 2 to 6 carbon atoms, or 2 to 5 carbon atoms. The silicate may be tetraethyl orthosilicate.

The molar ratio of iron to said silicate may be about 1:1 to about 1:50, or about 1:1 to about 1:45, or about 1:1 to about 1:40, or about 1:1 to about 1:35, or about 1:1 to about 1:30, or about 1:1 to about 1:25, or about 1:1 to about 1:20, or about 1:1 to about 1:18, or about 1:1 to about 1:16, or about 1:1 to about 1:15, or about 1:1 to about 1:12, or about 1:2 to about 1:12, more preferably about 1:5 to about 1:12.

The catalysts as defined above may be prepared according to the methods as defined above.

In a specific example, there is provided a one-pot synthesis method of iron-based nano-particulate catalyst promoted with metals such as Na, Mn and Ni. The method involves mixing an aqueous solution of Fe salt (e.g. $Fe(NO_3)_3$) with a surfactant (e.g. cetyl trimethyl ammonium bromide (CTAB)) in deionized water, followed by precipitation of the Fe phase as $Fe(OH)_2$ with a promoter base (e.g. NaOH). The resulting precipitate results in an Fe spinel phase with an amorphous Na phase, upon calcination in air. An appropriate zeolite, such as H—Y zeolite is then mixed physically with the nanostructured iron, resulting in a hybrid catalyst.

In another specific example, there is provided a one-pot synthesis method of structurally enhanced iron-based nano-particulate catalyst promoted with sodium. The method involves mixing an aqueous solution of Fe salt (e.g. $Fe(NO_3)_3$) with a surfactant (e.g. CTAB) in deionized water, followed by precipitation of the Fe phase as $Fe(OH)_2$ with a promoter base (e.g. NaOH). A suitable reagent such as tetraethyl orthosilicate (TEOS) or aluminium isopropoxide (AIP) is subsequently added to form an oxide matrix. If TEOS is added, $SiO_2$ is formed as a structural binder. The resulting precipitate results in an Fe spinel phase ($Fe_2O_3$) promoted with an amorphous Na phase, supported within an oxide matrix (e.g. $SiO_2$) upon calcination in air. An appropriate zeolite, such as H—Y zeolite is then mixed physically with the nanostructured iron, resulting in a hybrid catalyst.

Nano-sized Fe particles have been shown to provide enhanced performance for light olefin selection, and when combined with a high activity, Fe-based Fischer-Tropsch to olefin (FTO) process, is commercially attractive as light olefin yield per pass is maximized. Further, supporting the Fe-based catalysts on oxides such as $SiO_2$ and $Al_2O_3$ was shown to improve performance stability.

Fe-based catalysts have been paired with zeolites for Fischer-Tropsch (FT) synthesis, either as a Fe/zeolite-supported system, or a physically mixed Fe+zeolite system. When used in such a way, the paired zeolite, typically ZSM-5, has been observed to have a product distribution falling in the gasoline range, coupled with a high paraffin yield selectivity. In particular, the iron nanoparticles contain a high loading of alkali metals (~10-20 wt. %) of which the type is dependent on the metal hydroxide precipitant (e.g. Li, Na, K, Cs). For instance, Na can be incorporated into the iron phase through precipitation, with iron forming a dominant spinel phase which is not identified as $Fe_3O_4$ from X-ray diffraction (XRD) and extended X-ray absorption fine structure (EXAFS). This method was shown to have a higher than normal loading of alkali metals by incorporating them into the iron phase, allowing high olefinicity to occur concurrently with high activity of the catalyst.

The halogen anions present in the surfactant may also act as a promoter for the iron catalyst, where for example 1) Br was shown to both suppress hydrogenation over Ni and may have a similar effect to using S as a selective poison to enhance olefin selectivity, and 2) Br was shown to reduce $Fe(CO)_5$ to $Fe_5C_2$, an active carbide phase in FTO, and may have a similar role during dynamic phase changes in Fe-based catalysts during reactions. Retaining the alkali metals and halogens as promoters may also reduce the need for further waste water treatment during industrial synthesis, and may play a relevant role in cost analysis of the FTO technology.

There is also provided a process for the production of light olefins, the process comprising the steps of:

i) heating the catalyst as defined above in the presence of a gas comprising one or more oxides of carbon and hydrogen to activate said catalyst; and ii) contacting said activated catalyst of step (i) with a gas stream comprising one or more oxides of carbon and hydrogen to partially or fully convert said one or more oxides of carbon to said light olefins, said light olefins comprising between 2 to 4 carbon atoms, wherein methane is substantially absent from said light olefins, or constitutes less than 20% of said light olefins.

The oxides of carbon may be carbon monoxide (CO) or carbon dioxide ($CO_2$).

The step (i) may be carried out at a temperature of about 200° C. to about 350° C., or about 200° C. to about 340° C., or about 220° C. to about 300° C., or about 230° C. to about 300° C., or about 240° C. to about 300° C., or about 250° C. to about 300° C., or about 260° C. to about 300° C., or about 270° C. to about 300° C., or about 280° C. to about 300° C., more preferably about 290° C.

The step (ii) may be carried out at a temperature of about 200° C. to about 450° C., or about 220° C. to about 450° C., or about 240° C. to about 450° C., or about 260° C. to about 450° C., or about 280° C. to about 450° C., or about 300° C. to about 450° C., or about 300° C. to about 420° C., or about 300° C. to about 400° C., or about 320° C. to about 400° C., or about 330° C. to about 400° C., more preferably about 330° C. to about 390° C.

Step (i) may be carried out at a pressure of about 5 to about 30 bar, or about 5 to about 25 bar, or about 5 to about 20 bar, or about 5 to about 15 bar, or about 5 to about 10 bar, more preferably about 10 bar.

Step (ii) may be carried out at a pressure of about 5 to about 50 bar, or about 5 to about 45 bar, or about 5 to about 40 bar, or about 5 to about 35 bar, or about 5 to about 30 bar, or about 5 to about 25 bar, or about 10 to about 25 bar, or about 15 to about 25 bar, more preferably about 20 bar.

The space velocity of the gas stream in step (ii) may be about 1500 ml/g·h to about 5000 ml/g·h, or about 1500 ml/g·h to about 4500 ml/g·h, or about 1500 ml/g·h to about 4000 ml/g·h, or about 1500 ml/g·h to about 3500 ml/g·h, or about 1500 ml/g·h to about 3000 ml/g·h, or about 1500 ml/g·h to about 2500 ml/g·h, or more preferably about 2000 ml/g·h to 2500 ml/g·h.

The molar ratio of hydrogen to the one or more oxides of carbon in the gas may be about 4:1 to about 1:3, or about 3:1 to about 1:3, or about 2:1 to about 1:3, or about 2:1 to about 1:2, more preferably about 1:1.

The process may further comprise, prior to step (i), reducing the catalyst as defined above by contacting said catalyst with a stream of hydrogen gas.

The oxide of carbon in the gas stream of step (ii) may be substantially carbon dioxide.

The conversion of carbon dioxide to hydrocarbon products via the processes as defined above may be at least 20 mol C %, or at least 30 mol C %, or at least 40 mol C %, or at least 50 mol C %.

The yield of methane in the product stream obtained from the processes as defined above may be less than 15%, or less than 10%, or preferably less than 5% of the product gas stream. In addition, the concentration of carbon monoxide in the product gas stream may be less than 12%, or less than 10%, or less than 8%, or less than 5%, or less than 1%.

Additionally, the processes as defined above may yield olefin products of between 2 to 4 carbon atoms in an amount of at least 5 mol %, or between 5 to 90%, or between 5 to 85%, or between 5 to 80%, or between 5 to 75%, or between 5 to 70%, or between 5 to 65%, or between 5 to 60%, or between 5 to 55%, or between 5 to 50%, or between 5 to 45%, or at least between 5 to 40%.

The amount of hydrocarbons comprising 2 to 4 carbon atoms in the product gas may be at least 20 mol %, or at least 25 mol %, or at least 30 mol %, or at least 35%. Of this, at least 75%, or at least 80%, or at least 85 mol % are olefins comprising 2 to 4 carbon atoms.

BRIEF DESCRIPTION OF DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.

FIG. 1 shows the transmission electron microscope (TEM) images of A) FeNa sample prepared by precipitation of $Fe(NO_3)_3$ with NaOH, scale bar 20 nm, and B) magnification to show the Fe-based particulates, scale bar 10 nm. The microstructure is composed of smaller Fe nano-particles of 4-5 nm in size.

FIG. 2A shows the X-ray diffraction (XRD) diffraction patterns of FeNa prepared through two methods. The first was prepared at room temperature with no aging (202) while the second was prepared at 70° C. and left to age for 16 hours (204).

FIG. 2B shows the X-ray diffraction (XRD) diffraction patterns of FeNa (208) in comparison to the simulated pattern of $FeNa_2O_4$ (206).

FIG. 3 shows the extended X-ray absorption fine structure (EXAFS) of the FeNa catalyst ($Fe_2O_3$—Na) (302) showing the Fe—O coordination peak (308) and Fe—Fe coordination peak (310) that the Fe—Fe coordination peak is lacking a shoulder (312) typically seen in $Fe_2O_3$ (306) and $Fe_3O_4$ (304).

FIG. 4 shows the electron dispersive x-ray spectrum (EDS) of FeNa showing a uniform dispersion of A) Fe, B) Br, C) Na and D) O. O acts as a reference for the distribution of minority elements such as Na and Br. Scale bar is 2.5 μm.

FIG. 5 shows the electron dispersive x-ray spectrum (EDS) of FeNa—Mn, showing a uniform distribution of A) Fe, B) Br, C) Na, D) Mn and E) O. O acts as a reference for the distribution of minority elements such as Na and Br. Scale bar is 2.5 μm.

FIG. 6 shows the X-ray photoelectron spectroscopy (XPS) spectrum of FeNa showing the contribution from Br in the catalyst.

FIG. 7 shows the transmission electron microscope (TEM) images of s-FeNa where the Fe-based nanoparticles are well dispersed throughout a 90 wt. % silica matrix. Scale bar is 10 nm.

FIG. 8 shows the light olefin ratio (O/(O+P)) versus CO conversion for the FeNa catalyst ($Fe_2O_3$—Na) activated at different conditions. The performance of the catalyst may be improved through parametric optimization.

FIG. 9 shows the comparison of long term stability between FeNa ($Fe_2O_3$—Na) catalyst with Fe/CNF (carbon nanofibers) from the prior art. The inventive catalyst continues to improve in performance after 170 hours, while the performance of the benchmark (prior art) catalyst dropped to less than half its initial performance after 100 hours.

EXAMPLES

Non-limiting examples of the invention will be further described in greater detail by reference to specific Examples, which should not be construed as in any way limiting the scope of the invention.

Example 1: General Synthesis

Three general classes of catalysts are disclosed:
1) Hybrid Nanostructured Fe-Zeolite Catalysts In one example, the present disclosure provides a method of producing hybrid nanostructured Fe-zeolite catalysts. The method begins by mixing a salt of Fe, such as $Fe(NO_3)_3$, with a surfactant, such as cetyl trimethylammonium bromide (CTAB), in deionized $H_2O$ to form a well-mixed solution. An alkali base, such as NaOH, is subsequently used to precipitate the iron in the solution. The precipitate is collected without washing via centrifugation and dried in air before calcination at 550° C. for 2 hours to obtain Fe-based spinel nanoparticles. This method produces Na-promoted nano-particles of about 4-5 nm in size in a single precipitation and calcination step without the need for any washing protocol to remove the Na cation and offers good performance in light olefin (C2-C4) selectivity and yield. These nanoparticles are then physically mixed with a zeolite, such as ZSM-5, to form the hybrid catalyst. The hybrid catalyst Fe oxide catalyst is then activated in syngas at 10 bar and 290° C. for 24 hours, followed by tracking the performance of the catalyst at 370° C. and 20 bar in flowing syngas with $H_2$/CO=1. Upon reaching a high activity (>90 C mol. % CO conversion), the temperature and/or $H_2$/CO ratio is tuned to maximize light olefin yield.

2) Hybrid Nanostructured Fe-Zeolite Catalysts Promoted with X

In another example, the present disclosure provides a method of producing hybrid nanostructured Fe-zeolite catalysts promoted with X, where X=Ni, Mn, Mg, Ca, La, Co, Li, K, Ce, or any of the combination thereof. The method of producing nano-sized Fe-based catalysts is carried out by mixing a salt of Fe, such as $Fe(NO_3)_3$, and a promoter salt, such as $Mn(NO_3)_2$, with a surfactant, such as CTAB, in deionized $H_2O$ to form a well-mixed solution. An alkali base, such as NaOH, is subsequently used to precipitate the iron in the solution. The precipitate is collected via centrifugation without washing and dried in air before calcination in air at 500° C. for at least 2 hours or 5 hours to obtain Fe-based spinel nanoparticles. This method produces X-promoted nano-particles of about 4-5 nm in size in a single precipitation and calcination step without the need for any washing protocol to remove the X cation and offers good performance in light olefin (C2-C4) selectivity and yield. These nanoparticles are then physically mixed with a zeolite, such as ZSM-5, to form the hybrid catalyst. The hybrid catalyst is then activated in syngas at 10 bar and 290° C. for 24 hours, followed by tracking the performance of the catalyst at 370° C. and 20 bar in flowing syngas with $H_2$/CO=1. Upon reaching a high activity (>90 C mol. % CO conversion), the temperature and/or $H_2$/CO ratio ca be tuned to maximize light olefin yield.

3) Hybrid Nanostructured Supported-Fe-Zeolite Catalysts, Optionally Promoted with X In another example, the present disclosure provides a method of producing hybrid nanostructured supported-Fe-zeolite catalysts, which may or may not be promoted with X, where X=Ni, Mn, Mg, Ca, La, Co, Li, K, Ce or any of the combination thereof. The method begins by mixing a salt of Fe, such as $Fe(NO_3)_3$, a salt of X if promotion with X is desired, and cetyl trimethyl ammonium bromide (CTAB) in deionized water. NaOH solution is used to precipitate the iron and X from the solution. Tetraethyl orthosilicate (TEOS) and hydrolyzed to form a structural promoter in the form of $SiO_2$, to form a silica matrix. The precipitate is then collected via centrifugation without washing and dried in air before being calcined in air at 500° C. or higher for at least 2 hours. This method produces X-promoted nano-particles of about 4-5 nm in size in a single precipitation and calcination step without the need for any washing protocol to remove the Na cation and offers good performance in light olefin (C2-C4) selectivity, yield and enhanced stability. The supported Fe-based particles are then physically mixed with a zeolite, such as ZSM-5, to form the hybrid catalyst. The hybrid catalyst is then activated in syngas at 10 bar and 290° C. for 24 hours, followed by tracking the performance of the catalyst at 370° C. and 20 bar in flowing syngas with $H_2$/CO=1. Upon reaching a high activity (>90 C mol. % CO conversion), the temperature and/or $H_2$/CO ratio can be tuned to maximize light olefin yield.

Example 2: Fe-Zeolite Hybrid Catalyst (FeNa)

Fe-zeolite hybrid catalyst (FeNa+H—Y) was prepared by first mixing 10.81 g of $Fe(NO_3)_3 \cdot 9H_2O$ with 10 g CTAB in 400 ml deionized $H_2O$ to form a well-mixed solution. 4 g of NaOH in 80 ml deionized $H_2O$ was subsequently used to precipitate the iron in the solution. The suspension was allowed to age at room temperature for 5 minutes before collection of the precipitate via centrifugation. No washing of the precipitate was performed in order to allow the Na to remain as a promoter. The precipitate was then dried in air before calcination at 550° C. for 2 hours. This resulted in a FeNa catalyst with a Na promotion of about 10 wt. %. Subsequently, H—Y zeolites were physically mixed with FeNa in a 1:1 weight ratio to yield the hybrid catalyst.

The hybrid catalyst was transferred to a fixed bed reactor and reduced in flowing $H_2$. It was then activated in syngas at 10 bar and 290° C. for 24 hours, followed by tracking the performance of the catalyst at 370° C. and 20 bar in flowing syngas with $H_2$/CO=1 at a space velocity of 2,000 ml/g·h. Upon reaching a high activity (>90 C mol. % CO conversion), the temperature and/or $H_2$/CO ratio could be tuned to maximize light olefin yield.

High resolution transmission electron micrographs were acquired using a field emission transmission electron microscope (TEM) (Tecnai G2 TF20 S-twin, FEI Company) operated at 200 kV. FIG. 1A shows the transmission electron microscopy (TEM) images of the FeNa catalysts, where the nanoparticles are clustered together and can be made out clearly in magnified FIG. 1B.

X-ray diffraction (XRD) spectra were collected at room temperature using a Bruker D8 Advance diffractometer (Bruker AXS GmbH, Germany) equipped with Cu-Kα radiation source ($\lambda$=1.54056 Å) operated at 40 kV and 30 mA. The samples were scanned using Bragg-Brentano geometry within the range of $2\theta=10°-90°$. The crystal phase of the Fe-based particles is shown in FIG. 2 where the X-ray diffraction (XRD) patterns indicate an as-yet unidentified spinel structure. FIG. 2A shows the X-ray diffraction (XRD) diffraction patterns of FeNa with precipitation occurring at room temperature and without aging showing mixed phases of spinel and haematite (202), and at 70° C. with 16 hours aging (204), where the spinel phase becomes dominant. It can be seen that aging promotes the formation of the spinel phase ($FeNa_2O_4$), which can be seen from the lack of peaks around 33°, 35.8°, and 54°.

FIG. 2B shows the X-ray diffraction (XRD) diffraction patterns of FeNa (208) in comparison to the simulated pattern of $FeNa_2O_4$ (206). FIG. 2B shows the good correspondence between measured and simulated patterns with an error range for peak position of about ±1%. The measured spectrum was smoothed to improve the signal-to-noise ratio and then $LiMn_2O_4$ was used as a starting structure, where Li was replaced with Na and Mn was replaced with Fe. A periodic unit cell was constructed and discrete Fourier transform (DFT) performed to obtain its ground state using Quantum Espresso. The XRD pattern for $FeNa_2O_4$ was subsequently simulated using Visualization for Electronic and Structural Analysis (VESTA).

X-ray absorption spectra (XAS) of Fe K edge was recorded at the X-ray Absorption Fine Structure For Catalysis (XAFCA) beamline at the Singapore Synchrotron Light Source. The samples were first mixed and ground thoroughly with boron nitride, followed by pressing into a small circular disc with a diameter of 1 cm. XAS spectra of the catalysts were then collected in He at room temperature.

Extended X-ray absorption fine structure analysis (EXAFS) analysis was done by Athena software. EXAFS of FeNa (302) in FIG. 3 showed that the Fe—O coordination peak (308) may be found at a radial distance of 1.4 Å, while the first Fe—Fe coordination peak (310) may be found at 2.6 Å. The second Fe—Fe coordination peak (312) may be found at around 3.1 Å, which is typical for $Fe_3O_4$ (304) and existed as shoulder for $Fe_2O_3$ (306) due to less Fe in the chemical composition. FIG. 3 revealed a missing Fe—Fe coordination peak (312) for FeNa ($Fe_2O_3$—Na)(302) typically seen in $Fe_2O_3$ (306) and $Fe_3O_4$ (304) phases, which may suggest a substitution of the Fe atom with that of another element, hypothetically Na.

Elemental composition analysis of the FeNa catalyst was performed using electron dispersive x-ray spectrum (EDS), shown in FIG. 4. The EDS shows uniform dispersion of positively identified Fe (FIG. 4A), Br (FIG. 4B), Na (FIG. 4C) and O (FIG. 4D) contributions. EDS was carried out using field emission scanning electron microscopy (FE-SEM, JEOL JSM 6700) at a beam energy of 5 keV with Oxford instrument EDS system.

Table 1 shows the performance of FeNa and FeNa combined with various zeolites, at 370° C., 20 bar, $H_2/CO=1$ and gas hourly space velocity (GHSV) of 2,000 ml/g·h.

Specifically, FeNa catalyst were pelletized at 40 kN and sieved to 250-500 μm particles. Then 0.5 g of the FeNa catalyst was loaded to a fixed bed reactor for testing after mixing with SiC at a volume ratio=1:1. Reduction was carried out at 600° C. for 6 hours in $H_2$ and ambient pressure at a space velocity of 2000 ml/(g·h). Activation was carried out at 290° C. for 24 hours in CO and $H_2$ with $H_2/CO$ ratio=2 at 10 barg and a space velocity of 2000 ml/(g·h). The CO reaction was carried out at 370° C. in CO and $H_2$ with $H_2/CO$ ratio=2 at 20 barg and a space velocity of 2000 ml/(g·h).

The reaction data in Table 1 shows an improvement in activation time (from 40 hours to between 10-16 hours), as well as a general increase in C2-C4 hydrocarbon selectivity. It would appear that H—Y zeolites can change the hydrocarbon distribution by cracking C5+ to shorter chain hydrocarbons. Further, olefinicity was also improved when FeNa was combined with zeolites such as H—Y (80) and ZSM-5 (80). Higher $SiO_2$-to-$Al_2O_3$ ratio results in higher olefinicity from both H—Y and ZSM-5 zeolites Yields for light olefins over FeNa+H—Y (80) increased over that for FeNa alone, shown also in Table 1. This shows that the activity, selectivity and olefinicity can be tuned by mixing the catalyst with various zeolites.

TABLE 1

Performance of hybrid FeNa + zeolite combination for FTO at 370° C., 20 bar, 2000 ml/g.h and $H_2/CO = 1$.

| Catalyst | TOS (hr) | Conv. (mol C %) | $CH_4$ (mol C %) | $CO_2$ (mol C %) | Hydrocarbon distribution (mol C %) | | | LO/(O + P) (mol C %) | | | LO Yield (mol C %) |
|---|---|---|---|---|---|---|---|---|---|---|---|
| | | | | | $CH_4$ | C2-C4 | C5+ | C2 | C3 | C4 | |
| FeNa | 40 | 92 | 8 | 43 | 20 | 49 | 31 | 59 | 89 | 83 | 20 |
| FeNa + H-Y (5) | 16 | 94 | 12 | 43 | 28 | 54 | 18 | 30 | 77 | 43 | 15 |
| FeNa + H-Y (80) | 16 | 95 | 8 | 42 | 21 | 51 | 28 | 62 | 89 | 80 | 22 |
| FeNa + ZSM-5 (30) | 16 | 94 | 8 | 43 | 21 | 55 | 24 | 51 | 87 | 53 | 19 |
| FeNa + ZSM-5 (80) | 10 | 92 | 7 | 43 | 17 | 49 | 34 | 67 | 90 | 80 | 20 |
| FeNa + SAPO11 | 12 | 93 | 10 | 39 | 24 | 53 | 23 | 42 | 85 | 62 | 20 |
| FeNa + SAPO34 | 16 | 95 | 10 | 41 | 24 | 51 | 25 | 33 | 78 | 53 | 16 |

TOS: Time on Stream
O: Olefin
P: Paraffin
LO: light olefin
The numbers in the brackets in the name of catalyst indicate the $SiO_2/Al2O_3$ mole ratio for the zeolites.

Similar hybrid systems reported in the art typically exploits ZSM-5 for its shape and size selectivity and targets the production of paraffinic hydrocarbons in the gasoline range. In contrast, the present system aims to maximize light olefin selectivity and yield. A comparison with similar hybrid systems is shown in Table 2. Olefinicity is dramatically enhanced with the hybrid FeNa-ZSM-5 system.

calcination at 550° C. for 2 hours. This resulted in a FeNa—Mn catalyst with a Na promotion of about 10 wt. % and an Fe to Mn ratio of about 9. Subsequently, H—Y zeolites were physically mixed with FeNa—Mn in a 1:1 weight ratio to yield the hybrid catalyst.

The hybrid catalyst was then transferred to a fixed bed reactor and reduced in flowing $H_2$. An activation protocol

TABLE 2

Performance of FeNa + ZSM-5 combination compared with similar systems in the art
Reaction of FeNa + ZSM-5 was carried out at 370° C., 20 bar, 2000 ml/g.h and H/CO = 1.

| Catalyst | Conv. (mol C %) | CH4 (mol C %) | CO2 (mol C %) | Hydrocarbon distribution (mol C %) | | | LO/(O + P) (mol C %) | | | LO Yield (mol C %) |
|---|---|---|---|---|---|---|---|---|---|---|
| | | | | CH4 | C2-C4 | C5+ | C2 | C3 | C4 | |
| FeNa + ZSM-5 (30) | 94 | 8 | 43 | 21 | 55 | 24 | 51 | 87 | 53 | 19 |
| Fe-Cu-K/ZSM-5 (25)* | 81 | | 38 | 18 | 25 | 57 | ← | 40 | → | 5 |
| FeNa + ZSM-5 (80) | 92 | 7 | 43 | 17 | 49 | 34 | 67 | 90 | 80 | 20 |
| Fe + ZSM-5 (80)** | 96 | | 43 | 17 | 35 | 48 | ← | 0 | → | 0 |

*Reaction carried out at 300° C., 10 bar, 2000 ml/g.h and $H_2$/CO = 2 (comparative example)
**Reaction carried out at 300° C., 10 bar, 2240 ml/g.h and $H_2$/CO = 1 (comparative example)

The examples in Table 2 were precipitated with NaOH (with the exception of Fe—Cu—K/ZSM-5 (25), which was precipitated with KOH, and Fe+ZSM-5 (80), which was precipitated with $NH_4OH$) using nitrate salts of Fe and Cu. The examples were then mixed with ZSM-5 for testing. FeNa (inventive catalyst) is $Fe_2O_3$—Na, while Fe (comparative example) is purely $Fe_2O_3$ and Fe—Cu (comparative example) is mixture of iron oxide and copper oxide.

Example 3: Mn Promoted Fe-Zeolite Hybrid Catalyst

Mn promoted Fe-zeolite hybrid catalyst (FeNa+H—Y) was prepared by first synthesizing a Mn promoted FeNa (FeNa—Mn) catalyst by mixing 9.73 g of $Fe(NO_3)_3.9H_2O$ and 0.67 g of $Mn(NO_3)_2.4H_2O$ with 10 g CTAB in 400 ml deionized $H_2O$ to form a well-mixed solution. 4 g of NaOH in 80 ml deionized $H_2O$ was subsequently used to precipitate the metals in the solution. The suspension was allowed to age at room temperature for 5 minutes, before collection of the precipitate via centrifugation. No washing of the precipitate was performed in order to allow the Na to remain as a promoter. The precipitate was then dried in air before flowing syngas in the ratio $H_2$/CO=1, 10 bar and 290° C. for 24 hours was used to activate the catalyst. Finally, an induction period was observed by tracking the performance of the catalyst at 370° C. and 20 bar in flowing syngas with $H_2$/CO=1 at a space velocity of 2,000 ml/g·h. Upon reaching a high activity (>90 C mol. % CO conversion), the temperature and/or $H_2$/CO ratio may be tuned to maximize light olefin yield.

FIG. 5 shows the electron dispersive x-ray spectrum (EDS) mapping of the constituent atoms in the FeNa—Mn catalyst. The images show a well dispersed and uniform distribution of Fe (FIG. 5A), Br (FIG. 5B), Na (FIG. 5C) and Mn (FIG. 5D), as well as the oxygen content present in oxide form (FIG. 5E). X-ray photoelectron spectroscopy (XPS) was performed on a VG ESCALAB 250 spectrometer equipped with a monochromatic Mg Kα radiation source. All binding energies were adjusted to the line position of C1s at 284.6 eV as a reference.

FIG. 6 shows the XPS spectrum of FeNa for Br, where the binding energy suggests that Br is present in the form of bromate and can be reduced to bromide during the reduction process in $H_2$. The reduced bromide may then play a role in $Fe_5C_2$ formation.

TABLE 3

Performance of FeNa-Mn at 370° C., 20 bar, H/CO = 1 and GHSV of 12,000 ml/g.h with and without the mixing with H-Y zeolite.

| Catalyst | TOS (hr) | Conv. (mol C %) | CH4 (mol C %) | CO2 (mol C %) | Hydrocarbon distribution (mol C %) | | | LO/(O + P) (mol C %) | | | LO Yield (mol C %) |
|---|---|---|---|---|---|---|---|---|---|---|---|
| | | | | | CH4 | C2-C4 | C5+ | C2 | C3 | C4 | |
| FeNa-Mn | 24 | 95 | 8 | 42 | 21 | 49 | 30 | 54 | 88 | 79 | 20 |
| FeNa-Mn + H-Y (80) | 4 | 95 | 8 | 41 | 22 | 52 | 26 | 49 | 86 | 68 | 20 |

17

Table 3 shows that the hybridization with H—Y zeolite improved the FTO reaction by shortening the activation time by 6 fold, while increasing the light hydrocarbon fraction.

Example 4: FeNa Catalyst in Silica Matrix

FIG. 7 shows a transmittance electron microscopy (TEM) micrograph of s-FeNa where the Fe-based nanoparticles are well dispersed throughout a 90 wt. % silica matrix.

Typically, 10.81 g of the iron precursor $Fe(NO_3)_3.9H_2O$ were dissolved in 400 ml of deionized (DI) $H_2O$ and mixed with 10 g of cetyl trimethylammonium bromide (CTAB). The precipitating reagent was prepared by dissolving 4 g of NaOH in 80 ml of DI $H_2O$, of which 60 ml was subsequently added instead of the usual 80 ml in order to obtain spherical Fe nanoparticles through pH control. It should be noted that precipitating with 80 ml of NaOH solution would have yielded rod-like Fe structures. The encapsulation of the iron catalyst was done by first preparing the unsupported catalyst up till the precipitation step (i.e. before the step of drying in air and calcination) according to Example 2, followed by the addition of $SiC_8H_{20}O_4$ (TEOS) according to the weight percent required. For example, $10Fe_2O_3@SiO_2$ which comprises 10 wt % $Fe_2O_3$ required 143 ml of TEOS dissolved in 200 ml of ethanol. The TEOS was allowed to undergo hydrolysis for at least 8 hours before the mixture was centrifuged and dried at 80° C. for 48 hours before use.

Example 5: Performance Comparison

The performance of the inventive catalyst was compared to a benchmark comparative example.

TABLE 4

Performance of FeNa, FeNa + H-Y, 10FeNa@SiO2 in comparison to a comparative example, Fe(Na + S)/CNF

| Catalyst | CO Conv. (mol C %) | CO2 Sel. (mol C %) | CH4 (mol C %) | C2-C4 Olefin (mol C %) | C2-C4 Paraffins (mol C %) | C5+ (mol C %) | LO Yield (mol C %) | O/(O + P) (mol C %) |
|---|---|---|---|---|---|---|---|---|
| FeNa | 92 | 43 | 20 | 38 | 11 | 31 | 20 | 77.6% |
| FeNa + H-Y (80) | 95 | 42 | 21 | 39 | 12 | 28 | 22 | 76.5% |
| 10FeNa@SiO2 | 61 | 44 | 32 | 30 | 25 | 13 | 11 | 54.5% |

TABLE 4-continued

Performance of FeNa, FeNa + H-Y, 10FeNa@SiO2 in comparison to a comparative example, Fe(Na + S)/CNF

| Catalyst | CO Conv. (mol C %) | CO2 Sel. (mol C %) | CH4 (mol C %) | C2-C4 Olefin (mol C %) | C2-C4 Paraffins (mol C %) | C5+ (mol C %) | LO Yield (mol C %) | O/(O + P) (mol C %) |
|---|---|---|---|---|---|---|---|---|
| Fe(Na + S)/CNF* | 87 | 42 | 10 | 37 | 23 | 30 | 19 | 61.7% |

Conv. stands for conversion
Sel. stands for selectivity
*Comparative example from:
Torres Galvis, Hirsa M., et al. "Iron particle size effects for direct production of lower olefins from synthesis gas." Journal of the American Chemical Society 134.39 (2012): 16207-16215.

The comparative example was made by an impregnation method and supported on carbon nanofibers (CNF), whereas the inventive catalyst was formed by precipitation.

The inventive catalysts in Table 4 (first and second rows) were observed to have better olefin percentage (O/(O+P)) than the comparative example (fourth row), with the inventive catalyst having significantly higher olefin percentage.

The above was further supported by FIG. 8 which shows the light olefin ratio (O/(O+P)) versus CO conversion for the inventive catalyst FeNa ($Fe_2O_3$—Na) activated at different conditions. The performance of the catalyst was shown to be improved through parametric optimization. FIG. 9 further shows the comparison of long term stability between $Fe_2O_3$—Na with Fe/CNF from the prior art. The inventive catalyst continues to improve in performance after 170 hours, while the performance of the benchmark (prior art) catalyst dropped to less than half its initial performance after 100 hours.

Table 4, FIG. 8 and FIG. 9 show that the inventive catalysts were able to achieve similar if not higher olefin selectivity compared to the comparative example, similar if not higher activity compared to the comparative example, and a milestone light olefin (LO) yield of 20%.

Example 6: CO2 to Olefins

The use of the catalyst for the conversion of $CO_2$ to olefins was also investigated. FeNa catalyst washed with deionized water were pelletized at 40 kN and sieved to 250-500 μm particles. Then 0.5 g of the FeNa catalyst was loaded to a fixed bed reactor for testing after mixing with SiC at a volume ratio=1:1. Reduction was carried out at 580° C. for 6 hours in $H_2$ and ambient pressure at a space velocity of 2000 ml/(g·h). Activation was carried out at 300 HC for 4 hours in CO and $H_2$ with $H_2$/CO ratio=2 at 10 barg and a space velocity of 2000 ml/(g·h). The $CO_2$ reaction was carried out at 350° C. in $CO_2$ and $H_2$ with $H_2$/$CO_2$ ratio=3 at 15 barg and a space velocity of 5500 ml/(g·h).

The catalytic performance of the FeNa catalyst for $CO_2$ to olefins reaction is presented in Table 5.

TABLE 5

Performance of the FeNa catalyst for $CO_2$ to olefins reaction, with $X(CO_2)$ being the conversion of $CO_2$, and $S(CH_4)$ and $S(CO)$ being the selectivity towards $CH_4$ and CO respectively.

| TOS (hrs) | X(CO2) mol C % | S(CH4) mol C % | S(CO) mol C % | Light Olefin (LO) Yield | % of Olefins C2 | C3 | C4 | C2-C4 | Hydrocarbon distribution CH4 | C2-C4 | C5+ |
|---|---|---|---|---|---|---|---|---|---|---|---|
| 2 | 42 | 11 | 14 | 9.1 | 79 | 89 | 84 | 84.5 | 13 | 30 | 57 |
| 4 | 44 | 12 | 13 | 10.0 | 79 | 90 | 83 | 84.6 | 14 | 30 | 56 |
| 6 | 44 | 13 | 12 | 10.2 | 80 | 90 | 84 | 85.0 | 14 | 31 | 55 |

TABLE 5-continued

Performance of the FeNa catalyst for $CO_2$ to olefins reaction, with $X(CO_2)$ being the conversion of $CO_2$, and $S(CH_4)$ and $S(CO)$ being the selectivity towards $CH_4$ and CO respectively.

| TOS | $X(CO_2)$ mol | $S(CH_4)$ | $S(CO)$ | Light Olefin (LO) | % of Olefins | | | | Hydrocarbon distribution | | |
|---|---|---|---|---|---|---|---|---|---|---|---|
| (hrs) | C % | mol C % | mol C % | Yield | C2 | C3 | C4 | C2-C4 | $CH_4$ | C2-C4 | C5+ |
| 8 | 44 | 13 | 12 | 9.9 | 80 | 90 | 85 | 85.5 | 13.8 | 29.7 | 56.5 |
| 10 | 45 | 13 | 12 | 10.2 | 80 | 91 | 85 | 85.8 | 14.1 | 30.0 | 55.9 |
| 18 | 45 | 13 | 11 | 10.2 | 81 | 91 | 86 | 86.6 | 13.8 | 29.3 | 56.8 |
| 20.0 | 46 | 13 | 11 | 10.4 | 81 | 91 | 88 | 87.4 | 14.0 | 29.4 | 56.6 |
| 22.0 | 46 | 13 | 11 | 10.6 | 82 | 91 | 85 | 86.5 | 14.2 | 30.2 | 55.6 |
| 26.0 | 46 | 13 | 11 | 10.8 | 82 | 91 | 85 | 86.5 | 14.1 | 30.6 | 55.3 |

The above shows that the FeNa catalyst can achieve a light olefin yield of 10.8% at a $CO_2$ conversion of 46% with very high percentage of olefin in C2-C4 and relatively low $CH_4$ and CO selectivity. Further optimization to improve the olefin yield may be possible.

INDUSTRIAL APPLICABILITY

The hybrid nanoparticle iron catalyst as disclosed herein may be used in Fischer Tropsch synthesis to convert CO, $CO_2$ or a mixture of CO and $CO_2$ and $H_2$ as feedstock to produce light olefins. The catalyst may be useful in the process of synthesizing light olefins, whereby the process may have high selectivity for light olefins over methane, longer chain olefins or paraffins, and the catalyst may have a significantly shorter activation time. The method of preparing the catalyst as disclosed herein may allow for the catalyst to be prepared by co-precipitation of an iron nanoparticle catalyst with a basic salt solution, making the preparation of the catalyst facile. Further, the process as disclosed herein may be used in the preparation of light olefins, whereby the process may be highly selective for light olefins. The catalyst may also be useful in converting CO and/or $CO_2$ feedstocks to other hydrocarbons such as alcohols and C5+ hydrocarbons.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

The invention claimed is:

1. A hybrid iron nanoparticle catalyst comprising:
   i) 30 wt. % to 70 wt. % of nanoparticles in oxide form comprising (a) iron, (b) at least one metal M selected from the group consisting of alkali metals, alkaline earth metals, transition metals of groups 3 to 7 or 9 to 11 of the Periodic Table of Elements, lanthanides, and combinations of M thereof, and (c) bromate; and
   ii) 70 wt. % to 30 wt. % of an aluminosilicate zeolite or silicoaluminophosphate zeolite, based on a total weight of the catalyst,
   wherein said nanoparticles have a diameter of 2 nm to 50 nm, and a total wt. % of the nanoparticles and zeolite is 100 wt. %.

2. The catalyst of claim 1, wherein said metal M comprises 10 wt. % to 50 wt. % based on a weight of the nanoparticles.

3. The catalyst of claim 1, wherein the nanoparticles adopt a spinel crystalline phase, or a spinel crystalline phase having the formula $FeM_2O_4$, or wherein the aluminosilicate zeolite is selected from pentasil zeolite or faujasite zeolite, or wherein the silicoaluminophosphate zeolite is selected from the group consisting of SAPO 11 or SAPO 34.

4. The catalyst of claim 3, wherein the pentasil zeolite or faujasite zeolite is selected from the group consisting of zeolite X, ZSM-5, zeolite Y, ZSM-12, ZSM-22, and HY zeolite.

5. The catalyst of claim 1, wherein a mole ratio of alumina to silica in the zeolite is about 1:2 to 1:90, or wherein a weight ratio of the zeolite to the iron nanoparticle is about 1:0.5 to 1:2.

6. The catalyst of claim 1, wherein the nanoparticles further comprise a transition metal of groups 3 to 7 and 9 to 11 of the Periodic Table of Elements, or wherein the nanoparticles further comprise a $SiO_2$ matrix.

7. The catalyst of claim 6, wherein a molar ratio of iron to the transition metal is 1:1 to 50:1.

8. A hybrid iron nanoparticle catalyst prepared according to a method comprising:
   i) mixing an iron salt with an aqueous surfactant comprising a bromide anion to form a mixture;
   ii) adding a basic salt solution comprising a salt of alkali metals to the mixture of step (i) to form a precipitate;
   iii) heating the precipitate of step (ii) in the presence of air and oxygen; and
   iv) mixing the precipitate of step (iii) with an aluminosilicate or a silicoaluminophosphate zeolite to yield a hybrid iron catalyst,
   wherein the catalyst comprises:
   i) 30 wt. % to 70 wt. % of nanoparticles in oxide form comprising iron, alkali metals, and bromate; and
   ii) 70 wt. % to 30 wt. % of an aluminosilicate zeolite or silicoaluminophosphate zeolite, based on a total weight of the catalyst,
   wherein said nanoparticles have a diameter of 2 nm to 50 nm, and a total wt. % of the nanoparticles and zeolite is 100 wt. %.

9. A process for the production of light olefins, the process comprising a step of:
   i) heating the catalyst of claim 1 in the presence of a gas comprising one or more oxides of carbon and hydrogen to activate said catalyst; and
   ii) contacting said activated catalyst of step (i) with a gas stream comprising one or more oxides of carbon and hydrogen to partially or fully convert said one or more oxides of carbon to said light olefins, said light olefins comprising between 2 to 4 carbon atoms,
   wherein methane is substantially absent from said light olefins, or constitutes less than 20% of said light olefins.

10. The process of claim 9, wherein step (i) is carried out at a temperature of 200° C.-350° C., or wherein step (ii) is carried out at a temperature of 200° C.-450° C., or wherein step (i) is carried out at a pressure of 5-30 bar, or wherein step (ii) is carried out at a pressure of 5 to 50 bar, or wherein the space velocity of the gas stream in step (ii) is 1500 ml/g·h to 5000 ml/g·h, or wherein the molar ratio of hydrogen to the one or more oxides of carbon in the gas is 4:1 to 1:3.

11. The process of claim 9, further comprising, prior to step (i), reducing the catalyst by contacting said catalyst with a stream of hydrogen gas.

\* \* \* \* \*